(12) United States Patent
Warriner

(10) Patent No.: US 11,752,684 B2
(45) Date of Patent: Sep. 12, 2023

(54) INDUCTIVELY HEATED MOLD SYSTEM

(71) Applicant: Blockwise Engineering LLC, Tempe, AZ (US)

(72) Inventor: Jeremiah J. Warriner, Tempe, AZ (US)

(73) Assignee: Blockwise Engineering LLC, Tempe, AZ (US)

(*) Notice: Subject to any disclaimer, the term of this patent is extended or adjusted under 35 U.S.C. 154(b) by 0 days.

(21) Appl. No.: 17/772,673

(22) PCT Filed: Nov. 29, 2021

(86) PCT No.: PCT/US2021/061020
§ 371 (c)(1),
(2) Date: Apr. 28, 2022

(87) PCT Pub. No.: WO2022/115708
PCT Pub. Date: Jun. 2, 2022

(65) Prior Publication Data
US 2023/0122890 A1   Apr. 20, 2023

Related U.S. Application Data

(60) Provisional application No. 63/118,890, filed on Nov. 28, 2020.

(51) Int. Cl.
*B29C 49/48* (2006.01)
*B29C 49/08* (2006.01)
*H05B 6/10* (2006.01)
*B29L 31/00* (2006.01)

(52) U.S. Cl.
CPC .......... *B29C 49/4823* (2013.01); *B29C 49/08* (2013.01); *H05B 6/105* (2013.01); *B29C 2049/4825* (2013.01); *B29C 2049/4838* (2013.01); *B29C 2049/4853* (2013.01);
(Continued)

(58) Field of Classification Search
CPC ..... H05B 6/105; B29C 49/08; B29C 49/4823; B29C 2049/4853; B29C 2049/4825; B29C 2049/4894; B29C 2049/4838; B29L 2031/7543
See application file for complete search history.

(56) References Cited

U.S. PATENT DOCUMENTS 5,736,171 A   4/1998  McGrevy
6,613,262 B1  9/2003  Arend
(Continued)

*Primary Examiner* — Monica A Huson
(74) *Attorney, Agent, or Firm* — Invention To Patent Services; Alex Hobson

(57) ABSTRACT

An inductively heated mold system enables rapid heating of the mold and rapid cooling to reduce thermal cycling times by employing an inductive coil in a heater module that inductively heats a ferromagnetic layer configured on the mold body, such as around the outside perimeter of the mold body. A cooling channel may be configured between the inductive coil and the ferromagnetic layer on the mold body to allow a fluid to be passed between the mold body and the heater module to rapidly cool the mold body for removal of the molded part. A plurality of heater modules may be employed that can be coupled together such that the cooling fluid passes through the coupled cooling channels from one module to a second module. In this way heater modules can be combined to provide an inductively heated mold system for a variety of mold body sizes, or lengths.

21 Claims, 8 Drawing Sheets

(52) U.S. Cl.
CPC .............. *B29C 2049/4894* (2013.01); *B29L 2031/7543* (2013.01)

(56) References Cited

U.S. PATENT DOCUMENTS

2006/0219709 A1  10/2006  Kagan
2009/0239023 A1   9/2009  Olin et al.

INDUCTIVELY HEATED MOLD SYSTEM

CROSS REFERENCE TO RELATED APPLICATIONS

This application claims the benefit of priority to U.S. provisional patent application No. 63/118,890, filed on Nov. 28, 2020.

BACKGROUND OF THE INVENTION

Field of the Invention

The invention relates to inductively heated mold systems and in particular mold system requiring rapid cooling between heating cycles.

Background

Many molding systems require molds to be heated to processing temperature before molding can begin. Time required to heat the mold between cycles is part of the overall processing time for the production. Minimizing this time is important as it directly impacts the cost to make the molded parts. In addition, some molds require the molds to be cooled in between molding cycles, to remove the part without deformation or damage, for example. In these systems, both rapid cooling and rapid heating are even more important. Heating rods and cooling channels are often configured in the mold body or heating modules are configured around the mold body to heat the mold body through conductive heating. A heating module or a heating jacket may be employed to heat the mold from the outside in through conductive heating. The gap distance between the heater module and the mold body therefore must be kept very low, to promote rapid heating. This tight gap between the mold body and heater module often leads to longer cooling times, as thermal expansion causes these parts to engage thereby preventing removal of the mold body from the heater module. Therefore, the heating and cooling cycles may be longer than desired.

SUMMARY OF THE INVENTION

The invention is directed to inductively heated mold systems and in particular to a mold system that enables rapid heating of the mold and rapid cooling to reduce thermal cycling times. An exemplary inductively heated mold system employs an inductive coil in a heater module that inductively heats a ferromagnetic layer configured on the mold body, such as around the outside perimeter of the mold body. The material of the mold body may be a material that has high thermal conductivity, like copper, or a copper alloy. Using a material with high thermal conductivity will reduce internal temperature variations. A cooling channel may be configured between the inductive coil and the ferromagnetic layer on the mold body to allow a fluid to be passed between the mold body and the heater module to rapidly cool the mold body for removal of the molded part. An exemplary inductively heated mold system may comprise a plurality of heater modules that can be coupled together such that the cooling fluid passes through the coupled cooling channels from one module to a second module. In this way the number and/or size of the heater modules can be combined to provide an inductively heated mold system for a variety of mold body sizes, or lengths.

An exemplary inductively heated mold system may be configured for expansion and elongation of a parison into a balloon. Medical balloon catheters are used in a wide range of minimally invasive diagnostic and therapeutic procedures, including dilating vessels, opening blockages, delivering stents, and more. The balloon portion of the balloon catheter is formed from a parison, a polymeric tubular rod having tapering ends. The tube is heated and an inflation fluid, such as air, is forced into one end to expand the balloon radially while the balloon is stretched along a length axis to elongate the balloon. This procedure forms a thin-walled balloon that has increased tensile strength. This expanded balloon is then attached to a catheter and typically compressed by a sheath for insertion into the body, such as into the vascular system. The process to make the expanded balloons requires the parison to be heated to an expansion temperature within a mold body to a threshold temperature before stretching and expanding. The mold body then has to be cooled below a threshold temperature to remove the expanded balloon from the mold body. Quick thermal cycles are desired in this process.

An exemplary inductively heated mold system configured for balloon catheter balloon processing may comprise a mold body having a cylindrical portion for receiving the parison. One end of the parison may be coupled with an inflation fluid source, such as compressed air or nitrogen. The other end of the parison may be pinched or otherwise blocked to allow the inflation fluid to radially expand the parison. The mold body may have a ferromagnetic layer configured around the outside surface that is configured to be heated by an inductive heater in a heater module. A cooling channel gap between the inductive heater and the ferromagnetic layer, such as along the cylindrical outer surface of the mold body may enable rapid cooling by the flow of water directly onto the mold body. The cooling channel has an offset distance, a dimension of the cooling channel aligned between the ferromagnetic layer and the heater module and/or inductive coil, and this offset distance may be effectively large to enable quick cooling. This offset distance may be about 1 mm or more, about 2 mm or more, about 3 mm or more, about 4 mm or more, about 5 mm or more, about 6 mm or more, about 8 mm or more and any range between and including the values provided. This large offset distance would not be practical for conductive heating via a heater module but does allow for very rapid cooling due to the volume of cooling fluid that can be passed over the mold body surface. In addition, this larger offset distance ensures that thermal expansion does not prevent removal of the mold body from the heater module.

Another advantage is that the mold body does not require any heating rods or cooling channels configured directly therein. This makes processing much quicker and easier and the mold body simple has to be placed in the heater module and removed without attachment to cooling fluid conduits or electrical heaters.

The ferromagnetic layer on the mold body is a material that can be heated by the inductive coil, or by rapid alteration of the magnetic fields. Induction heating takes place in an electrically conducting object (not necessarily magnetic steel) when the object is placed in a varying magnetic field. Induction heating is due to the hysteresis and eddy-current losses which occur in magnetic materials such as iron, nickel, cobalt, gadolinium, dysprosium and alloys of these materials such as steel that contains specific iron or nickel. The ferromagnetic layer increases the efficiency of the inductive heating. A thin layer of ferromagnetic material bonded to a thermally conductive material, like copper or a copper alloy, has the benefit of both high inductive heating efficiency, and rapid heat transfer internal to the mold. Non-ferromagnetic materials can be heated via induction heating, but the efficiency is quite low, and the inductive drive system is more complex. Nickel may be a desired ferromagnetic layer due to high corrosion resistance properties. A ferromagnetic layer may be thin and may become very hot very quickly through induction heating. This very hot ferromagnetic layer then heats the mold body through conduction. This method of heating may be much quicker than conventional heating using a heater module coupled around the mold body. The temperature of the ferromagnetic layer may reach an effectively high temperature upon inductive heating. The thickness of the ferromagnetic layer may be thin, such as about 10 micrometers (μm) to about 500 μm thick, such as about 10 μm or more, about 100 μm or more, about 200 μm or more, about 300 μm or more, about 400 μm or more and any range between and including the thickness values provided.

An exemplary inductively heated mold system configured for balloon catheter balloon processing may have a mold body that forms an extended sleeve on one of both of the two ends of the cylindrical mold body. This extended sleeve may be configured to receive an end sleeve plug which may have an aperture to receive the tapered end of the parison. The end sleeve plug may be made out of a thermally conductive material, such as metal, that is heated by conductive heating from the extended sleeve. The end sleeve plug may comprise removed material, to enable quick heating of the end sleeve plug. For example, the end sleeve plug may have plug apertures extending into the end sleeve plug along the length axis, that reduce the mass considerably, such as by ⅕ or more, about ¼ or more, about ⅓ or more, about ½ or more and any range between and including the mass reductions provided. The extended sleeve may be much thinner than the mold body thickness over the main cylindrical extension, and the ratio of the thickness of the extended sleeve to the thickness of the mold body extension thickness may be about ¼ or more, about ⅓ or more, about ⅕, or more, about ¹⁄₁₀ or more, about ¹⁄₂₀ or more and any range between and including the values provided. The thickness of the extended sleeve and the mass reduction of the end sleeve plug may be configured to enable the mold body and end sleeve plug to heat substantially at the same rate. With heating of any part, there will be heat loss considerations on the ends or exposed surfaces and accounting form them can enable uniform heating. This thin extended sleeve will heat much more quickly than the mold body extension and will then transfer the heat to the end sleeve plug. This additional interface between the extended sleeve and the end sleeve plug and the associated resistance is overcome by the thinnest of the extended sleeve.

An insulating cap may be configured over the exposed end of the end sleeve plug to reduce heat loss and may be made out of a thermally insulating material, such as a material having a thermal conductively of no more than 0.5 W/(mK). An exemplary end insulating cap may be made out of a high temperature resistance polymer, such as a fluoropolymer.

An exemplary heating module of the inductively heated mold comprises an inductive coil that may be configured in a coil potting, such as an epoxy. The coil potting may be electrically insulating but may be thermally conductive. The inductive coil may be an electrically conductive coil, such as a copper coil that produces a magnetic field in the inductive heated layer. The inductive coil may be exposed to the cooling channel or may buried within the coil potting. The body of the heater module may be made out of metal or other thermally conductive material, to aid in cooling of the mold body between heating cycles.

The mold body may be made out of a thermally conductive and durable material, such as metal and may be aluminum, steel, copper, a metal alloy and the like. The mold body has to transfer heat from the ferromagnetic layer to the mold cavity and the part to be molded, such as a parison, therein. An exemplary mold body has a thermal conductivity of about 100 W/(m*k) or more, about 200 W/(m*k) or more.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
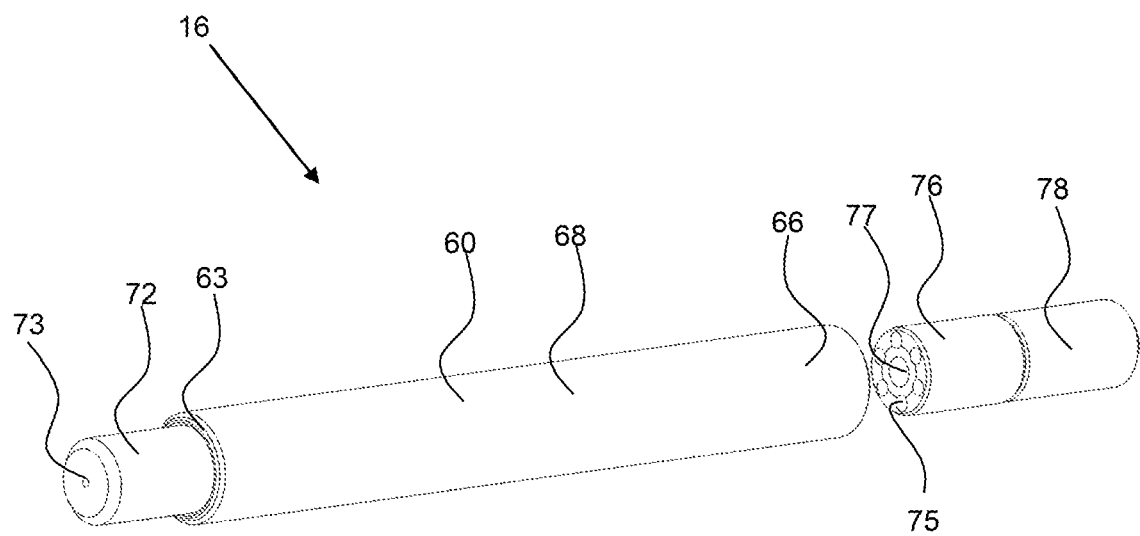
FIG. 1 shows a perspective view of an exemplary mold body assembly having a mold body, end sleeve plugs and insulator caps.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Referring to FIGS. 1 to 4, an exemplary inductively heated mold system 10 utilizes a mold body assembly 16 including a mold 60 that is configured for insertion into a heater assembly. The heater assembly may be modular, wherein two or more heater modules may be placed adjacent each other to heat the mold body. As shown, two heater modules 30, 40 are configured around the mold body assembly 16 to provide effective heating of the mold body and the moldable body therein. If the mold body were longer, an additional heater module could be added.

Figure 2:
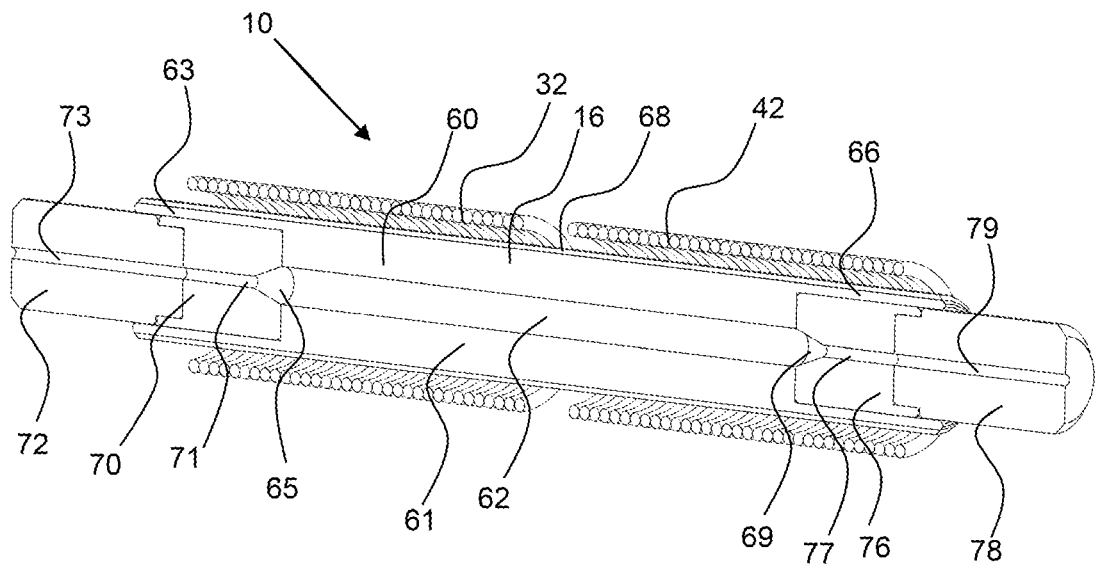
FIG. 2 shows a cross-sectional perspective view of an exemplary mold body assembly configured between inductive coils of a first and second modular heater assembly.
Figure 5:
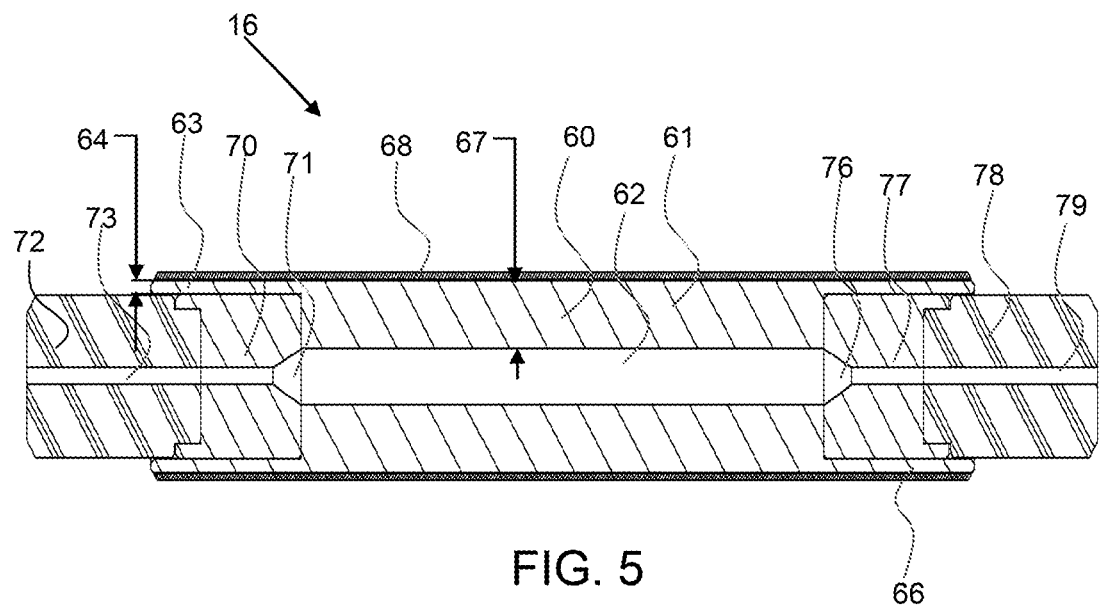
FIG. 5 shows a mold body assembly having a mold body with extended sleeves extending from the first and second ends with end sleeve plugs configured therein and insulator caps to seal and insulate the mold body; a conduit extends through the entire assembly.

As shown in FIGS. 1 and 2, an exemplary mold body assembly includes a mold body 60 that has a mold sleeve portion 61 that has a cylindrical conduit or mold cavity 62 extending therethrough from a mold cavity inlet 65 to a mold cavity outlet 69. The mold body has an inductively heated layer or ferromagnetic layer 68 that contains a ferromagnetic material. The inductive coils 32 and 42 will heat this ferromagnetic layer which will then heat the mold body 60 through conduction. The mold body has a first extended sleeve 63 and second extended sleeve 66 with a first end sleeve plug 70 and second end sleeve plug 76 configured therein. A sleeve plug will conduct heat from the extended sleeve as the extended sleeve heats very quickly due to the thin nature of the extended sleeve with respect to the wall thickness of the mold body in the mold sleeve portion 61. As described herein, the ratio of thickness of the mold sleeve portion to the thickness of the extended sleeve may be 5:1 or more, 10:1 or more and any range between and including the thickness ratios provided. The thickness 64 of the extended sleeve 63, and the thickness 67 of the mold sleeve portion 61 is shown in FIG. 5

A first end insulator cap 72 and second end insulator cap 78 are configured against the first end sleeve plug 70 and second end sleeve plug 76, respectively. The insulator caps are made of a thermally insulating material having a thermal conductively of less than 100 W/m*k and may be a high temperature resistant polymeric or ceramic material. As shown a portion of the first and second end insulator caps are inserted into an annulus of the first and second end sleeve plug respectively.

An aperture extends through the entire mold body assembly 16. The first end insulator cap 72 has a cap aperture 73 and the second end insulator cap 78 has a cap aperture 79. The first end sleeve plug 70 has a plug aperture 71, which may have a tapered portion for receiving and retaining a tapered portion of a parison. The second end sleeve plug 76 has a plug aperture 77 and may also have a tapered portion for receiving and retaining a tapered portion of a parison. The mold body has an inlet aperture 65 and outlet aperture 69 to the mold cavity 62. Again, the mold cavity may be cylindrical in shape. The apertures are aligned to receive and retain a parison for expanding the parison radially and also elongating the parison.

Figure 3:
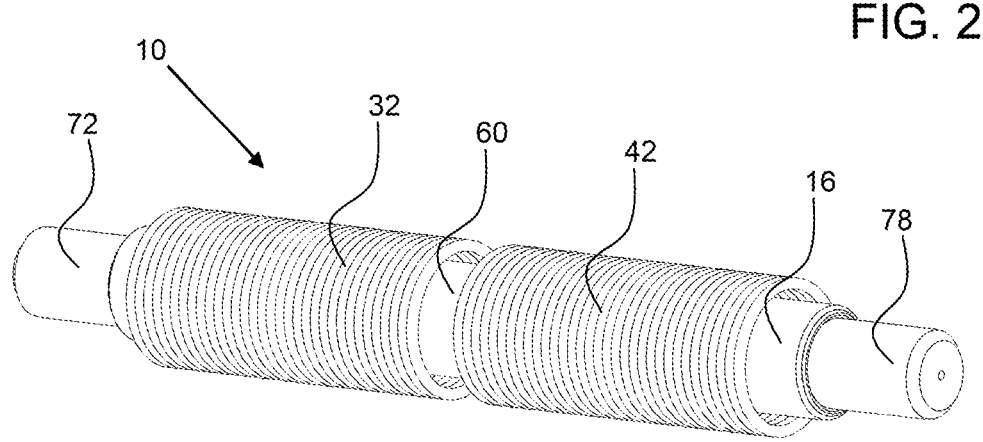
FIG. 3 shows a perspective view of an exemplary mold body assembly configured between inductive coils of a first and second modular heater assembly.
Figure 4:
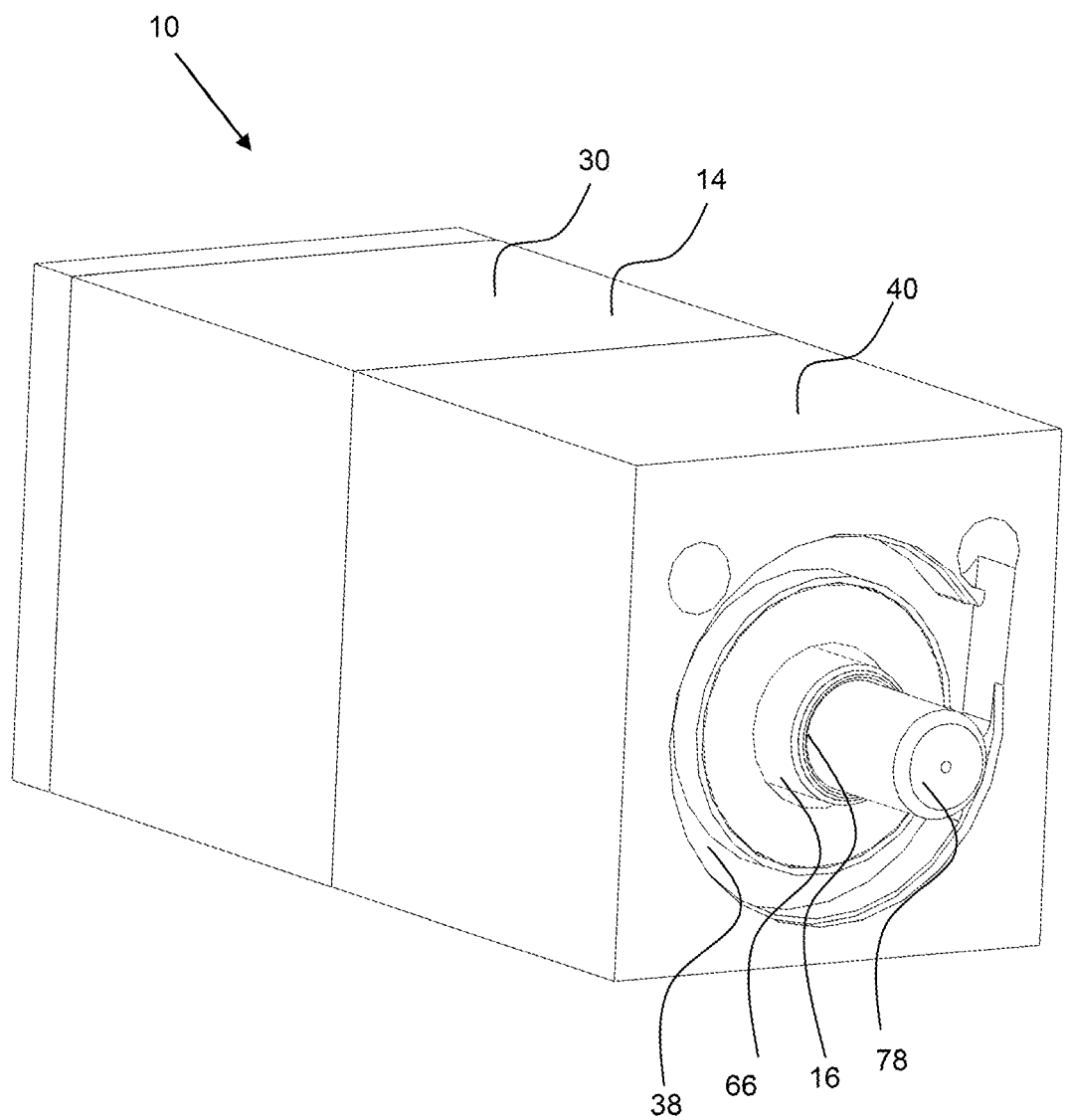
FIG. 4 shows a perspective view of an exemplary modular heater assembly comprising a first heater module and second heater module configured around a mold body assembly.

Referring to FIGS. 3 and 4, the exemplary mold body assembly 16 is configured within the inductive coils 32, 42 of a first heater module 30 and second heater module 40. The mold body assembly, or portion thereof, may be detachably attachable to the modular heater assembly 14 and may inserted into and removed from the mold aperture 38.

As shown in FIG. 1 the second end sleeve plug 76 has a plug aperture 77 and removed material apertures 75 to increase heating time. Also, as shown in FIG. 2, the first end sleeve plug 70 has a tapered aperture 71, and the first end insulator cap 72 has a first cap aperture 73 that are aligned to receive the parison. Likewise, the second end sleeve plug 76 has a plug tapered aperture 77, and the first end insulator cap 78 has a first cap aperture 79 that are aligned to receive the parison.

Figure 6:
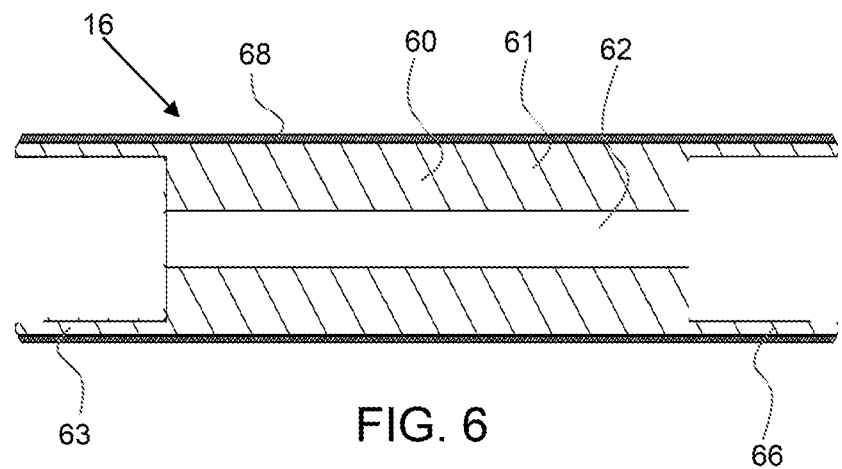
FIG. 6 shows the mold body assembly of FIG. 5 with the end sleeve plugs removed and the insulator caps removed from each end.
Figure 7:
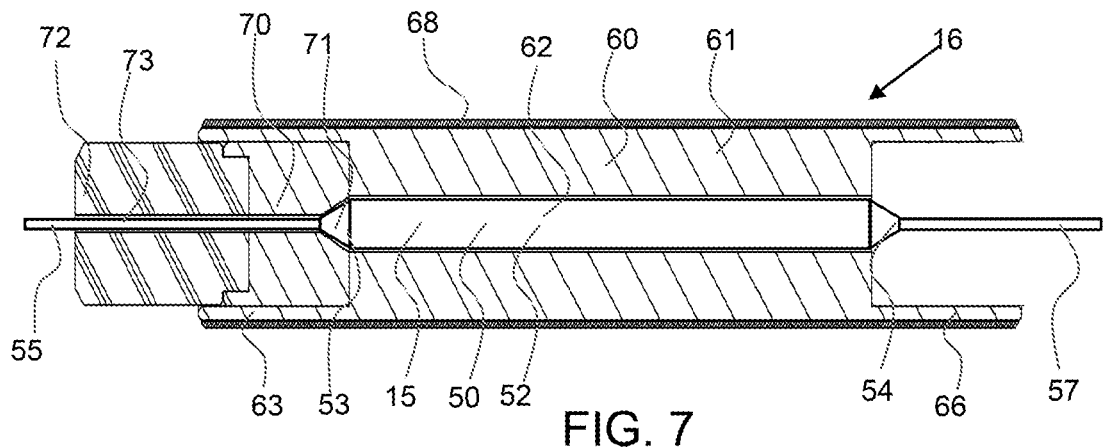
FIG. 7 shows the mold body assembly of FIG. 6, with a moldable body, a parison, configured within the mold cavity, and extending through the first end sleeve plug and the first end insulator cap.

Referring now to FIGS. 5 to 7, an exemplary mold body assembly 16 is configured to retain a parison 50, an exemplary moldable tube 15, with the first extension 55 of the parison extending through the first end sleeve plug 70 and out through the first end insulator cap 72. The parison has a first tapered end 53 retained in the tapered aperture 71 of the first end sleeve plug. The balloon extension 52 of the parison is configured within the mold cavity 62 of the mold body 60. As shown in FIG. 7, the parison may be configured in the first end of the mold assembly and then the second end sleeve plug and second end insulator cap may be configured over the second extension 57 and over the second tapered end 54 of the parison. Note is some embodiments, the first end may be fixed or coupled with the mold body thereby having one end for removal. Alternatively, the parison may be configured in the mold body assembly 16 and then the entire mold body assembly may be inserted into the modular heater assembly through the mold aperture.

Figure 8:
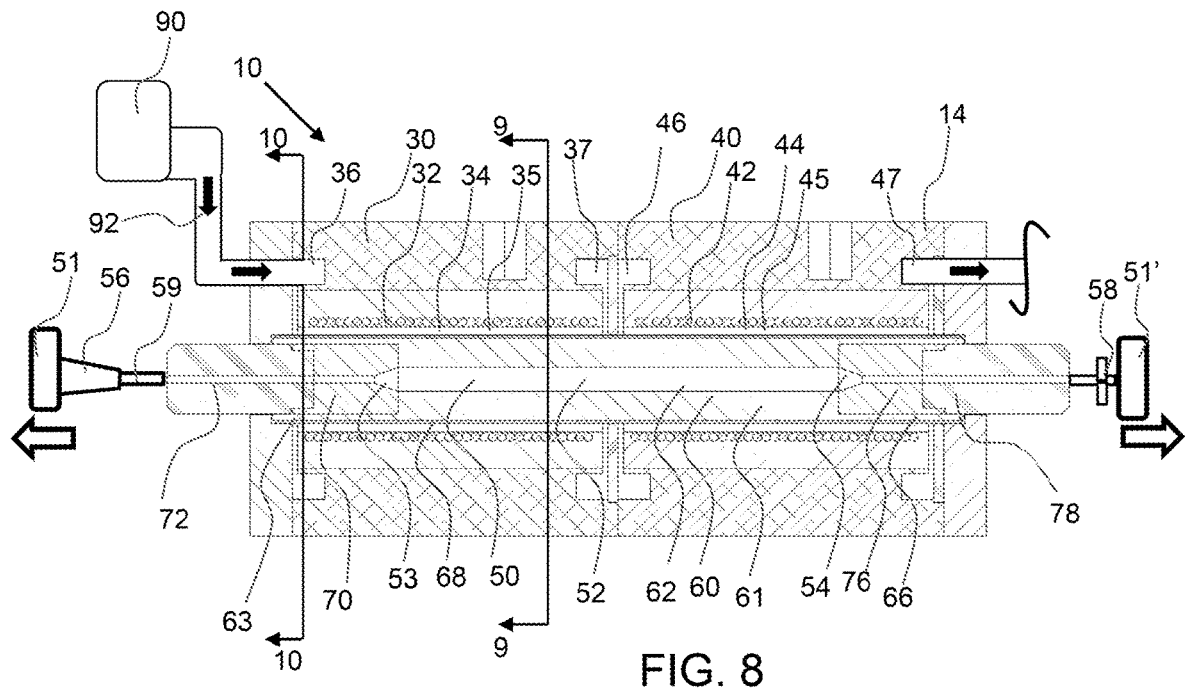
FIG. 8, shows an inductively heated mold assembly comprising two heater modules, each having an inductive coil, a mold body assembly configured within the heater modules and having an inductive heated layer.

As shown in FIG. 8, an exemplary inductively heated mold 10 has the mold body assembly 16 configured within the modular heater assembly 14. The moldable tube, or parison 50, is coupled with a fluid port 56 that is configured to fill the parison with a fluid for inflation and/or elongation. A clamp portion 58 of the parison is configured on the opposing second end of the fluid port. The inductive coils 32, 42 are configured in heater modules 30, 40, respectively and a cooling channel 34 is configured between the inductive coils and the ferromagnetic layer 68 of the mold body 60. In this embodiment, the cooling channel is a cooling anulus 35, extending radially around the cylindrically shaped mold body. A cooling fluid pump 90 pumps a flow of cooling fluid 92 from the cooling fluid inlet 36 to the cooling fluid outlet 37 in the first heater module 30 and from the cooling fluid inlet 46, through the cooling annulus 45 to the cooling fluid outlet 47 of the second heater module 40. Note that separate feeds or pumps may be used if the mold is long or large, wherein separate cooling fluid is introduced into each of the cooling fluid inlets. When two or more heating modules are coupled together, as shown, the cooling fluid may flow from one module to the next before exiting the modular heater assembly 14 out of the distal cooling fluid outlet 47. The inductively heated mold assembly enables a mold to be quickly heated and quickly cooled for faster throughput of molded bodies.

FIG. 8, shows an inductively heated mold assembly 10 comprising two modular heater assemblies 14, each having an inductive coil 32, a mold body 16 assembly configured within the heater modules 30, 40 and having a ferromagnetic layer 68. The first end sleeve plug 70 is configured within the first extended sleeve 63 of the first heater module 30 and the second end sleeve plug 76 is configured within second extended sleeve 66 of the second heater module 40. This extended sleeve plug has removed material apertures 75, as shown in FIG. 1, that enables the end sleeve plugs to heat more quickly due to the heat loss caused by the interface between the extended sleeve and the end sleeve plug. The removed material apertures, as shown in FIG. 1, enable the end sleeve plug to heat in about the same amount of time as the mold body between the extended sleeves. Also shown in FIG. 8 the first end insulator cap 72 and the second end insulator cap 78 are inserted into the first and second end sleeve plugs, respectively and thermally insulate the end sleeve plugs. The caps may be made out of a thermally insulating material, such as high temperature polymer, ceramic and the like. Also shown in FIG. 8 is are expanders 51, 51' configured on the first and second end of the parison, which are configured to stretch the parison, as indicated by the large arrows, after the parison has reached an expansion temperature. Note that the parison may be radially expanded by the pressure of the fluid introduced through the inflation port, or inflation fluid 59.

Figure 9:
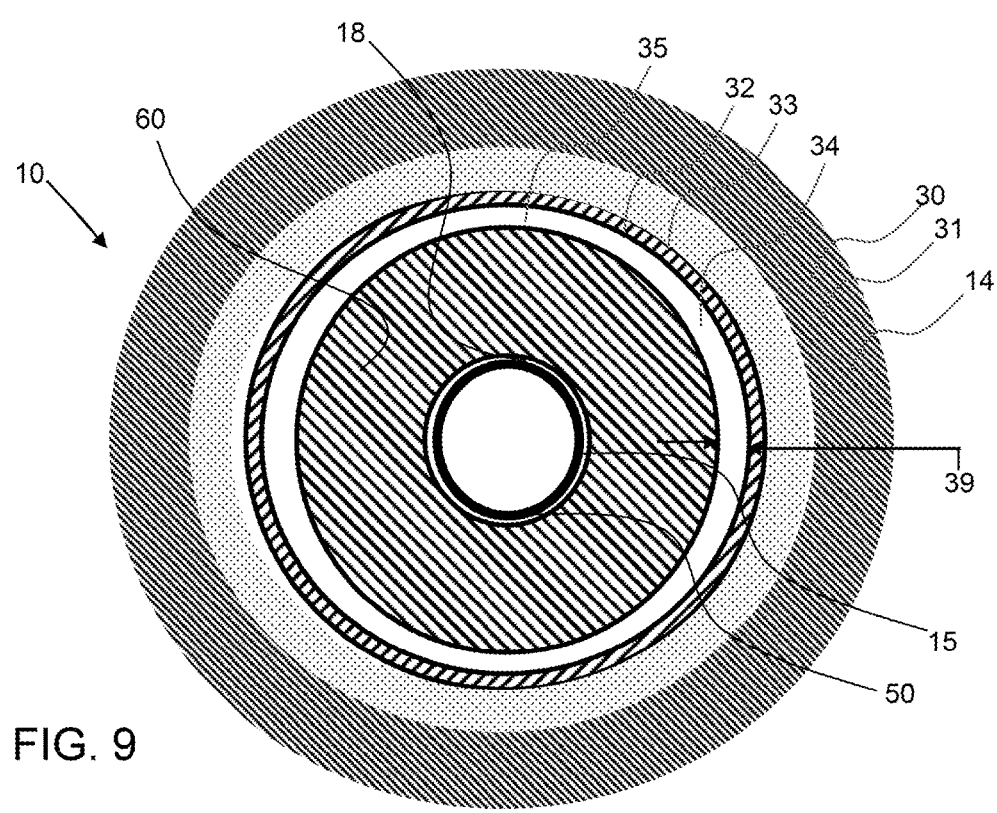
FIG. 9 shows a cross-sectional view of an inductively heated mold taken along line 9-9 in FIG. 8.

As shown in FIG. 9, an inductively heated mold assembly 10 comprises a cooling channel 34, a cooling anulus 35 having a cooling channel offset distance 39 extending radially in the direction between the inductive coil 32 and the mold body 60 or the ferromagnetic layer. The cooling channel offset distance is the dimension for cooling fluid to flow therethrough to quickly cool the mold body and end sleeve plug after a heating cycle. The inductive coil may be configured in a coil potting 33, an electrically insulating material, such as epoxy that secures the coil in place but insolates it electrically from the mold body and the heater module housing material 31, which may be thermally conductive to help cool the inductively heated mold body assembly 10 after a heating cycle. The cooling channel offset distance may be from the coil potting to the ferromagnetic material, or a cover layer configured thereover. As described herein the cooling channel offset distance or gap for the flow of cooling fluid may be 2 mm or more, about 3 mm or more, about 5 mm or more and any range between and including the channel offset distances provided. The parison 50, or moldable tube 15 has been expanded radially to form a balloon 18, as shown in FIG. 9.

Figure 10:
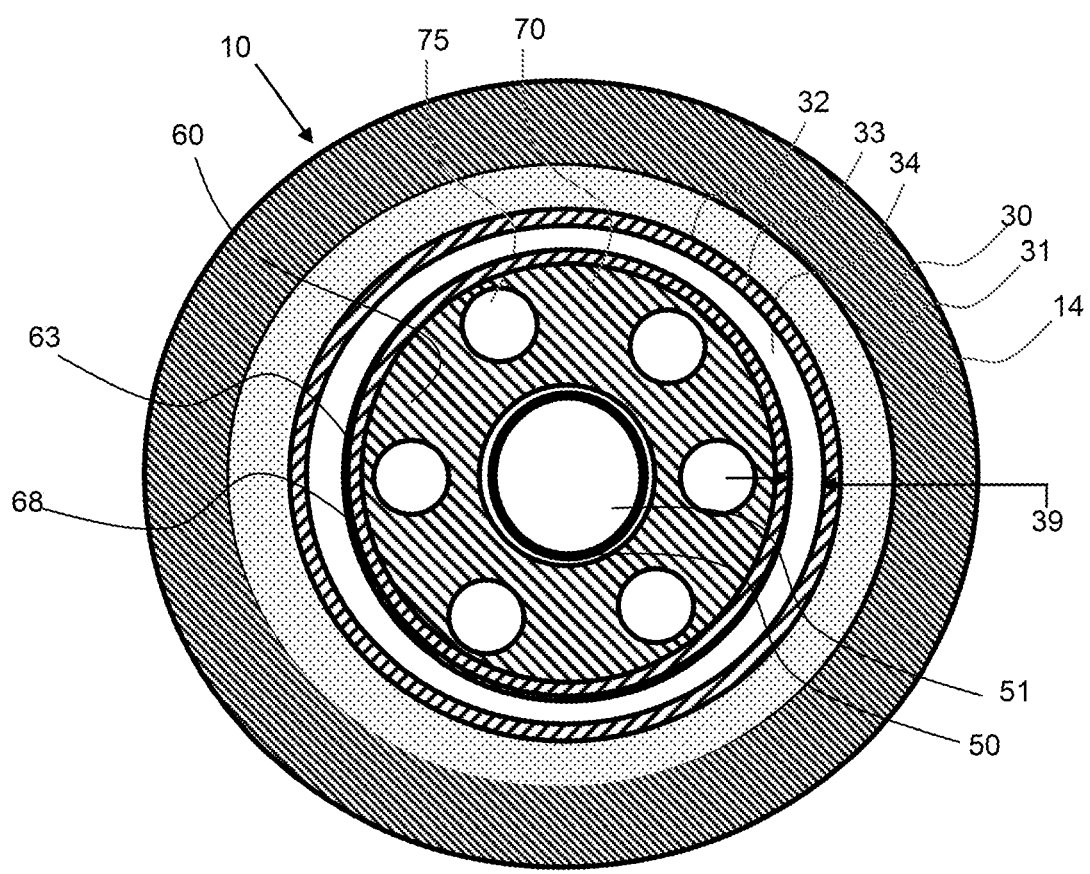
FIG. 10 shows a cross-sectional view of an inductively heated mold taken along line 10-10 in FIG. 8.

As shown in FIG. 10, the end sleeve plug 70 is configured within the first extended sleeve 63 having the inductively heated layer or ferromagnetic layer 68 thereon. The end sleeve plug has removed material 75, such as cylindrically shaped apertures to reduce the amount of material that has to be heated. The end sleeve plug may fit closely within the extended sleeve but the interface will cause resistance to heating and therefore, removed material may enable the temperature heating profile to match that of the mold body. The thickness of the extended sleeve 64 is shown and this may be a fraction of the thickness of the mold body extension. A mold body extension may be portion of the mold have substantially the same cross-section and may form a cylinder, as shown herein.

Figure 11:
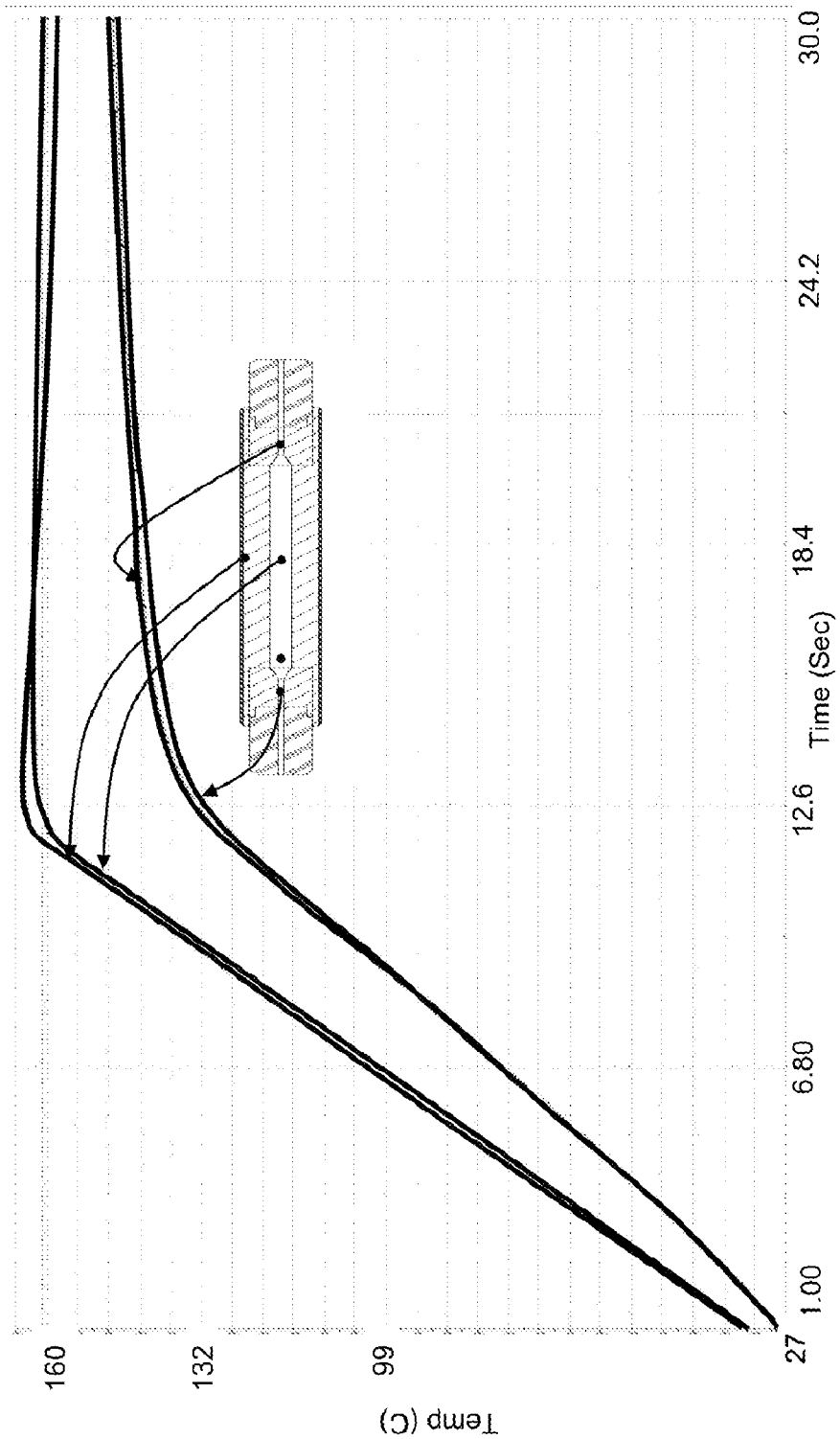
FIG. 11 shows a graph of mold temperature versus time for nodes along the mold body and plugs.

FIG. 11 shows a graph of mold temperature versus time for nodes along the mold body and end sleeve plugs. Note that the end sleeve plugs shown in FIG. 11 do not have removed material and they lag the heating of the mold body extension considerably.

Figure 12:
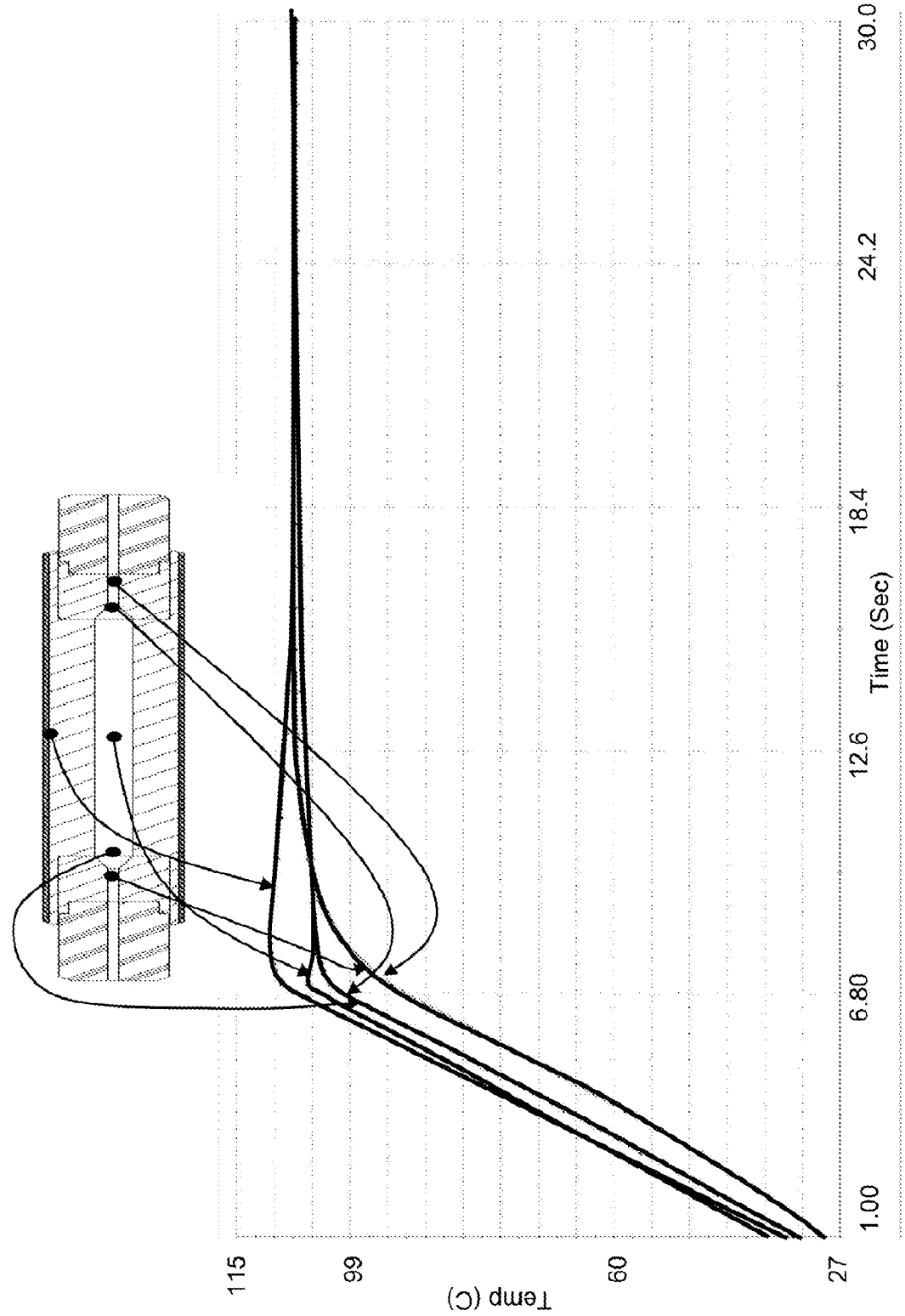
FIG. 12 show a graph of mold temperature versus time for when an inductively heated mold having an inductively heated layer or ferromagnetic layer that is used having extended sleeve portions of the mold with end sleeve plugs configured therein.

As shown in FIG. 12, the end sleeve plugs have removed material, as shown herein and the temperature profile is much closer to the temperature profile of the mold body extension.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A method of forming a balloon from a parison comprising:
 a) providing an inductively heated mold system comprising:
  first heater module comprising:
   a mold aperture;
   an inductive coil;
   a mold body assembly configured within the mold aperture and within the inductive coil and comprising:
    a mold body that is thermally conductive; and
    a mold cavity;
    a ferromagnetic layer configured around the mold body;
   a cooling channel between the ferromagnetic layer of the heater module and the inductive coil, wherein the cooling channel has an offset distance for a flow of a cooling fluid;
   wherein the ferromagnetic layer is configured to be heated by the inductive coil and wherein the ferromagnetic layer is configured to heat the mold body through thermal conduction;
 b) inserting a parison into the mold cavity;
 c) flowing electrical current through the inductive coil; wherein the ferromagnetic layer is heated inductively and heats the mold body;
 d) heating the parison;
 e) pumping an inflation fluid into the parison to expand the parison;
 f) stretching the parison;
 g) pumping a cooling fluid through the cooling channel to cool the mold;
 h) removing the parison from the mold cavity.

2. The method of claim 1, wherein the offset distance is at least 1 mm.

3. The method of claim 1, wherein the mold body is a thermally conductive metal.

4. The method of claim 1, wherein the mold body is made of material selected from the group consisting of, copper, silver gold, aluminum nitride, silicon carbide, tungsten, graphite, zinc, and composites thereof.

5. The method of claim 4, wherein the mold body has a thermal conductivity of at least 100 W/(m*k).

6. The method of claim 1, wherein the mold body cavity has an inlet aperture.

7. The method of claim 1, wherein the mold cavity has an inlet aperture and an outlet aperture.

8. The method of claim 7, comprising a plurality of heater modules that are configured for alignment wherein the mold cavity of the first heater module is aligned with a mold cavity of a second heater module.

9. The method of claim 1, comprising a plurality of heater modules that are configured for alignment wherein said flow of coolant flows from the first heater module to a second heater module with the module apertures in alignment for receiving a mold body.

10. The method of claim 9, wherein the first heater module has a cooling fluid inlet and a fluid cooling outlet and wherein the second heater module has a cooling fluid inlet and a fluid cooling outlet and wherein the cooling fluid outlet of the first heater module is in fluid communication with the cooling fluid inlet of the second heater module.

11. The method of claim 1, wherein the mold cavity has an inlet aperture and an extended sleeve configured around the inlet aperture; and
wherein mold body assembly comprises an end sleeve plug configured within the extended sleeve.

12. The method of claim 11, wherein the ferromagnetic layer is configured on the extended sleeve, wherein the ferromagnetic layer heats the extended sleeve and wherein the extended sleeve heats the end sleeve plug.

13. The method of claim 12, wherein the extended sleeve is a thermally conductive material.

14. The method of claim 11, wherein the sleeve plug has removed material apertures to increase a heating rate of the sleeve plug.

15. The method of claim 1, wherein the mold body comprises a first extended sleeve on a first end and a second extended sleeve on a second end and wherein the mold body assembly comprises a first sleeve plug located on said first end.

16. The method of claim 15, wherein the ferromagnetic layer is configured on the first extended sleeve, wherein the ferromagnetic layer heats the first extended sleeve and wherein the first extended sleeve heats the first end sleeve plug.

17. The method of claim 15, wherein the mold cavity comprises a second end sleeve plug located on said second end.

18. The method of claim 17, wherein the ferromagnetic layer is configured on the second extended sleeve, wherein the ferromagnetic layer heats the second extended sleeve and wherein the second extended sleeve heats the second end sleeve plug.

19. The method of claim 1, wherein a first end of the moldable tube is coupled with an inflation port.

20. The method of claim 19, wherein the moldable tube is sealed on a second sealed end.

21. The method of claim 1, wherein the parison has a cylindrical portion and a first tapered end and a second tapered end.

* * * * *